United States Patent [19]

Benedict et al.

[11] Patent Number: 5,011,913

[45] Date of Patent: Apr. 30, 1991

[54] DIPHOSPHONATE-DERIVATIZED MACROMOLECULES

[75] Inventors: James J. Benedict, Norwich, N.Y.; Charles R. Degenhardt, Cincinnati; James W. Poser, Fairfield, both of Ohio

[73] Assignee: The Procter & Gamble Company, Cincinnati, Ohio

[21] Appl. No.: 350,420

[22] Filed: May 11, 1989

Related U.S. Application Data

[62] Division of Ser. No. 750,103, Jun. 28, 1985, Pat. No. 4,830,847.

[51] Int. Cl.$^5$ .................... C07K 17/06; A61K 43/00; A61K 39/44; C07F 9/38
[52] U.S. Cl. .................................... 530/390; 530/391; 530/408; 530/409; 530/410; 530/345; 530/356; 424/1.1; 424/9
[58] Field of Search ..................... 424/1.1, 9; 530/390, 530/391, 405, 409, 402, 410, 356, 345, 408

[56] References Cited

U.S. PATENT DOCUMENTS

| | | |
|---|---|---|
| 4,337,240 | 6/1982 | Saklad .................................. 424/1.1 |
| 4,421,735 | 12/1983 | Haber et al. ......................... 424/1.1 |
| 4,472,509 | 9/1984 | Gansow et al. ...................... 436/548 |
| 4,693,884 | 9/1987 | Kleiner et al. ....................... 424/1.1 |
| 4,707,440 | 11/1987 | Stavrianopoulos .................... 435/6 |
| 4,839,467 | 6/1989 | Deutsch ................................ 534/10 |

OTHER PUBLICATIONS

Saha et al., "A Study of Protein-binding of $^{99m}$Tc-Methylene Diphosphonate in Plasma", 6 International Journal of Nuclear Medicine and Biology 201 (1979) 6(4):201-6 CA92(15):124160w.

Primary Examiner—Margaret Moskowitz
Assistant Examiner—Kay Kim
Attorney, Agent, or Firm—Milton B. Graff, IV; Karen F. Clark; David L. Suter

[57] ABSTRACT

Diphosphonate-derivatized macromolecules, such as proteins, suitable for use as technetium-99m-based scanning agents and as anticalcification agents are disclosed. The scanning agents are prepared by combining Tc-99m in a +3, +4 and/or +5 oxidation state with the diphosphonate-derivatized macromoleules. Also disclosed are pharmaceutical compositions containing these diphosphonate-derivatized macromolecules and methods for scintigraphic imaging using these diphosphonate-derivatized macromolecules labeled with Tc-99m.

6 Claims, No Drawings

DIPHOSPHONATE-DERIVATIZED MACROMOLECULES

This is a division of application Ser. No. 750,103, filed on June 28, 1985 now U.S. Pat. No. 4830847.

TECHNICAL FIELD

This invention relates to diphosphonate-derivatized macromolecules. Specifically, it relates to diphosphonate-derivatized macromolecules which may be radiolabeled with technetium-99 m.

BACKGROUND OF THE INVENTION

The detection and medical/diagnostic assessment of soft-tissue tumors currently requires a battery of relatively sophisticated diagnostic tests. Generally a physician will utilize every appropriate diagnostic test available when cancer is suspected. These tests utilize imaging equipment for a visual, internal examination and laboratory tests on potential tumor cells and secretions to determine the tumor burden. If a tumor is detected and appears to be malignant, a biopsy is performed to arrive at a diagnosis. Only the biopsy is taken as unequivocal evidence of malignancy.

The tests involving imaging equipment can be divided into two basic types: those involving an external energy source, such as X-rays or sound waves, and those involving an internal energy source, such as radioisotopes.

X-ray studies are the most useful tools in staging breast cancer. The method is also responsible for detecting the vast majority of lung cancer cases. Once a suspected site has been identified, precise radiographs can offer valuable information to the physician o the exact location and extent of tumors of the breast or lung. Unfortunately, by tee time the tumor is large enough to be detected by X-rays (1-2 cubic centimeters), the patient's prognosis may be relatively poor. In addition to the relatively low sensitivity of X-rays for soft-tissue tumors, serious concerns continue to be raised about the risks associated with this method's level of radiation exposure.

For breast cancer, the approximate location and size of the tumor can be obtained by ultrasound techniques. Ultrasound provides an image of the tumor from the pattern of echoes arising from high frequency sound waves impinging on the breast. Since ultrasonic examination of large sections of the body would be difficult to interpret and therefore of little value, this procedure is usually employed for breast examinations after a palpable lump has been detected.

Gallium (Ga-67) citrate is the only radiodiagnostic agent indicated for determining the presence and extent of certain soft-tissue tumors. Gallium has been shown to be of diagnostic utility in tumors of the lung and liver. In this procedure gallium is dosed intravenously; the gallium is then scanned by a gamma camera seeking an enhanced uptake of gallium in tumor tissue.

Gallium scanning suffers from several important drawbacks. The agent is neither tumor nor disease specific. Gallium will not only concentrate in many types of tumors (both benign and malignant) to some extent, but it also will seek out any localized infection. Because of these characteristics, the interpretation of scans obtained with gallium citrate is extremely difficult. The scans usually exhibit low contrast and diffuse areas of radioisotope concentration.

It has been discovered that proteins labeled with a radio-isotope are useful as radiotracers or radioscanners in humans. Examples include radiolabeled exogenous or autologous plasma protein for diagnostics of, e.g., pulmonary embolism; human serum albumin for blood pool imaging; radiolabeled tumor-specific antibodies for soft tumor imaging; radiolabeled enzyme proteins and hormone proteins for diagnosing metabolic and endocrinological disorders. The most widely used radionuclides are iodine-123, iodine-125, iodine-131, indium-111, gallium-67 and technetium-99 m. The iodine isotopes, being a halogen, can irreversibly be incorporated in protein molecules by relatively simple substitution chemistry. The iodine isotopes are less attractive for other reasons, especially the beta radiation emitted by these isotopes and the long half life (8 days) of iodine-131.

Technetium-99 m is generally recognized to be the most desirable radioisotope for radioscanning and radiotracing. Attempts to label proteins with technetium involve either chelating of the technetium ion by chelating groups inherently present in the protein molecule or derivatizing the protein molecules with a chelating group prior to labeling with the technetium. A chelate formed by technetium with chelating groups inherently present in the protein is by its nature not stable enough to prevent exchange of technetium with other protein ligands. Technetium-labeled proteins of this type, therefore, often lack the required biospecificity.

Chelator-derivatized proteins generally involve amino acetic acid compounds as chelators (e.g. ethylenediaminetetraacetic acid (EDTA) or DTPA). Proteins of this kind have been found to form strong chelates with indium-111.

Polyphosphonates, in particular diphosphonates, are generally recognized to be highly desirable ligands for chelating technetium. Prior to this invention proteins derivatized with diphosphonates have not been available. It is therefore an object of this invention to provide diphosphonate-derivatized proteins suitable for chelating technetium-99 m.

It is a further object of this invention to provide a method of labeling the diphosphonate-derivatized proteins utilizing technetium-99 m without denaturization or loss of biological activity of the protein.

It is still a further object of this invention to provide a protein-diphosphonate-technetium chelate, and to provide a method for scintigraphic imaging such as soft tumor imaging, in humans utilizing such chelates.

BACKGROUND ART

The use of radiolabeled proteins for soft tumor imaging is well known. Early attempts generally involved derivatization of proteins with iodine-123, iodine-125 or iodine-131. It is well-recognized, however, that of the conveniently available radionuclides, technetium has by far the best nuclear properties for diagnostic imaging (Eckelman et al., *Int. J. Appl. Radiation and Isotopes*, 28 (1977), pp. 67-82; Eckelman et al., *Cancer Research* 40 (1980), pp. 3036-3042).

Attempts have been made to label proteins with technetium. Several patents deal with "ligand exchange" and "direct labeling" techniques (U.S. Pat. No. 4,305,922, issued to Rhodes, Dec. 15, 1981; U.S. Pat. No. 4,311,688, issued to Burchiel et al., Jan. 19, 1982; U.S. Pat. 4,323,546, issued to Crockford et al., Apr. 6, 1982). Both methods are based on the inherent chelating properties of proteins. These complexes can be expected to be unstable in the presence of other proteins, and are therefore not suitable for soft tumor imaging.

Another approach has been the derivatization of proteins using bifunctional analogs of EDTA (Leung et al., *Int. J. Appl. Radiation and Isotopes*, 29 (1978), pp. 687-692; Sundberg et al., *J. Med. Chem*, 17 (1974), pp. 1364-1367). The chelating agents are linked to the protein by a diazo phenyl group. The compounds have been shown to chelate indium-111. This may be due to the fact that EDTA and similar chelators probably do not form very strong complexes with technetium (Deutsch et al., *J. Nucl. Med.*, 21 (1980), pp. 859-866).

U.S. Pat. No. 4,287,362, issued Sept. 1, 1981 to Yokoyama et al., discloses a bifunctional chelating agent specifically developed for labeling proteins with technetium. An albumin labeling efficiency of nearly 100% is reported and the compound provides "a much higher blood level for a longer period of time than conventional technetium-99 m labeled human serum albumin".

SUMMARY OF THE INVENTION

This invention comprises a diphosphonate-derivatized macromolecules of the formula

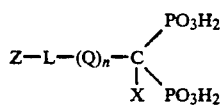

wherein
- Z is a macromolecule, selected from the group consisting of proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate) and poly(vinyl benzyl chloride), and further contains one or more reactive end groups selected from the group consisting of -NH$_2$, -COOH, -SH, CHO, -S—S-, -OH, phenol, guanidino, imidazole or indole and mixtures thereof,
- L is a linking moiety selected from the group consisting of

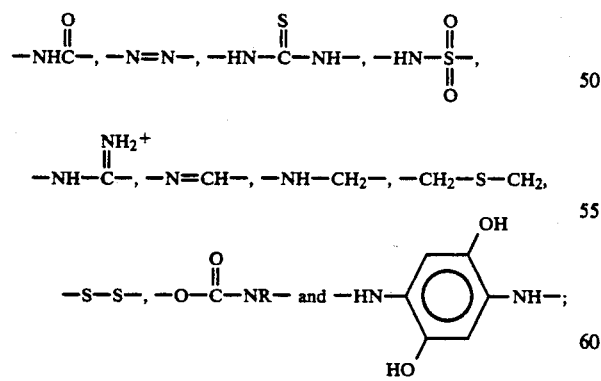

Q is a spacing group selected from the group consisting of substituted aryl, unsubstituted aryl or C$_1$ to C$_{12}$ alkyl, where n is 0 or 1; X is selected from the group consisting of H, OH, NH$_2$, substituted or unsubstituted amino, halogen or C$_1$-C$_4$ alkyl; and the pharmaceutically-acceptable salts of these derivatized macromolecules. These derivatized macromolecules are suitable for use as anticalcification agents which inhibits biological mineralization of bioprosthetic devices and soft contact lenses, and also as radiographic imaging agents useful for tumor imaging, radioassays, immunoassays, receptor binding assays or any other scintigraphic procedure where radiolabeled macromolecules would be used. The derivatized macromolecules are suitable for chelating heavy metal ions, in particular, technetium-99 m. Examples of derivatized proteins are derivatized blood proteins, derivatized enzymes, derivatized proteinaceous hormones, derivatized antibodies and antibody fragments, connective tissue and cytoskeletal proteins such as collagen, and myosin.

In its narrower aspect, this invention is directed to derivatized tumor-specific antibodies or antibody fragments chelated to technetium-99 m. This invention further provides a method of labeling the derivatized protein with technetium by *in situ* reduction of a pertechnetate solution without destroying the diphosphonate-protein bond or denaturing the protein leading to significant loss of biological activity. Technetium-protein chelates according to this invention are stable in the presence of plasma proteins; antibody technetium chelates retain their ability to bind their antigens; and the derivatized protein does not have an excessive affinity to bone tissue.

This invention further provides a method for scintigraphic imaging using diphosphonate-derivatized molecules chelated with technetium-99 m.

DETAILED DESCRIPTION OF THE INVENTION

This invention comprises a diphosphonate-derivatized macromolecule of the general formula:

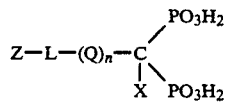

wherein
- Z is a macromolecule selected from the group consisting of proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate), poly(amide), poly(ethylene amine), poly(ethylene glycol), poly(propylene glycol), poly(vinyl acetate) and poly(vinyl benzyl chloride) preferably proteins, and further contains one or more reactive end groups selected from the group consisting of -NH$_2$, -COOH, -SH, CHO, -S—S, -OH, phenol, guanidino, imidazole or indole, and mixtures thereof;
- L is a linking moiety selected from the group consisting of

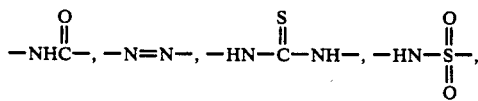

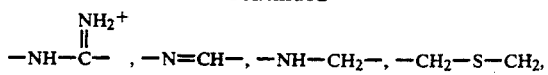

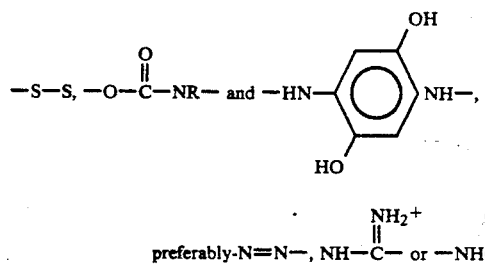

preferably -N=N—, NH—C(NH₂⁺)— or —NHC(O)—;

Q is a spacing group selected from the group consisting of substituted aryl, unsubstituted aryl or $C_1$ to $C_{12}$ alkyl, preferably an unsubstituted aryl, where n is 0 or 1; and X is selected from the group consisting of H, OH, $NH_2$, substituted or unsubstituted amino, halogen or $C_1$-$C_4$ alkyl, preferably H, OH, or $NH_2$; and the pharmaceutically-acceptable salts of these derivatized macromolecules.

By "pharmaceutically-acceptable salts" as used herein is meant salts of the diphosphonate-derivatized compounds which have the same general pharmacological properties as the acid form from which they are derived, and which are acceptable from a toxicity viewpoint. Pharmaceutically-acceptable salts include alkali metal (sodium and potassium), alkaline earth metal (calcium and magnesium), non-toxic heavy metal (stannous and indium), and ammonium and low molecular weight substituted ammonium (mono-, di and triethanolamine) salts. Preferred compounds are the sodium, potassium, and ammonium salts.

The geminal diphosphonate moieties of the present invention are linked to the macromolecule via the reactive groups which are part of the macromolecule. The reactive groups on macromolecules needed to link the diphosphonate to the macromolecule are carboxyl (COOH), thiol (SH), amino($NH_2$) phenol, aldehyde (CHO), alcohol ($CH_2OH$), guanidino, imidazole, indole and disulfide (-S—S) groups. The number of diphosphonates which link to the macromolecule depends upon the number of these reactive groups on the macromolecule. For scintigraphic imaging it is preferable to link at least one diphosphonate per macromolecule, and it is more preferable to link as many diphosphonates on the macromolecule as there are reactive groups, without causing significant loss of biological activity. For inhibition of biological mineralization, depending upon properties of the macromolecule, the optimal degree of derivatization will range from 1% to 90%. Those macromolecules which must retain their intrinsic biological activity will have a lower degree of derivatization (1% to 50%) due to the need to retain their optimal functional biological activity.

Suitable derivatizable macromolecules for use in this invention include proteins, such as antibodies, antibody fragments, human serum albumin, enzymes, proteinaceous hormones; water-soluble and water-insoluble polysaccharides, such as cellulose, starch, dextran and agar; acrylic homo- and copolymers, such a poly(arylate), poly(acrylamide), poly(methacrylate), poly(ethacrylate), poly(hydroxyalkylmethacrylate), poly(vinyl alcohol), poly(maleic anhydride) and poly(maleate); poly(amides); poly(ethylene imine); poly(ethylene glycol) and poly(propylene glycol); poly(vinyl acetate); and poly(vinyl benzyl chloride).

Other macromolecules suitable for use in the present invention are disclosed in Jakoby and Wichek (eds.), Methods in Enzymology., Vol. 34, pp. 53-76 (1974) and Mosbach (ed.) Methods in Enzymology, Vol. 44 pp. 11-148 (1976), both of which are incorporated by reference.

For scintigraphic imagings virtually any protein is suitable for use in this invention. However, certain proteins are particularly well-suited for specific utilities. For example, radiolabeled proteins for diagnosis of, e.g., pulmonary embolism; human serum albumin for blood pool imaging; radiolabeled enzyme protein and hormone proteins for diagnosing metabolic and endocrinological disorders; and radiolabeled antibodies or antibody fragments for soft tumor imaging.

The labeled antibodies and antibody fragments useful in the present invention are specific to a variety of tumor-associated antigens or markers. These markers are substances which accumulate in, on, or around tumor cells. They may be intracellular, cell surface or cytoplasmic markers. Tumor-specific markers and methods of raising antibodies to these markers are well known in the art. Such tumor specific markers are disclosed in Herberman, "Immunodiagnosis of Cancer", in Fleisher (ed.) "The Clinical Biochemistry of Cancer," p. 347 (Am. Assn. Clin. Chem. 1979) and in U.S. Pat. No. 4,331,647 to Goldenberg, issued May 25, 1982, and U.S. Pat. No. 4,361,544 to Goldenberg issued Nov. 30, 1982, all of which are incorporated by reference. Methods of raising antibodies in vitro are disclosed in Nezlin, "Biochemistry of Antibodies" pp. 255-286 (1970), incorporated by reference.

The diphosphonate moieties utilized in the present invention, absent a linking moeity (L), cannot form covalent bonds with the above-mentioned macromolecules since diphosphonates have no chemical affinity towards the protein. L is an atom, group of atoms or a chemical bond which attaches the geminal diphosphonate moiety separated via a spacer group, if appropriate, to the macromolecule. L is composed of a chemically-reactive moiety which can couple to a macromolecule by reaction with the specific reactive end group in the macromolecule.

The linking moiety, therefore, is the result of a reactive species on the diphosphonate forming a covalent bond with macromolecules. The determination of the appropriate linking moiety is dependent upon the availability of reactive groups on the macromolecule, i.e., carboxyl, sulfhydryl, disulfide, hydroxy, guandino, imidazole, indole, sulfhydryl, amino, phenol, aldehyde or alcohol groups. Another consideration, in the case of proteins, is whether or not modification of one or more of these reactive groups has a significant effect upon the biological activity of the protein. Significant loss occurs when the derivatized antibody will no longer localize sufficiently well on the target tissue.

Also within the scope of this invention is a procedure whereby the macromolecule is first pre-activated toward reacting with the diphosphonate. This is accomplished by derivatizing the acromolecule with a reagent bearing a substituent that would further react with the diphosphonate described in this invention.

The optimum linking moiety to be utilized, therefore, depends upon the reactive end group on the macromolecule to which the diphosphonate moiety is to be attached.

For example, utilizing proteins for illustration, when the reactive group is phenolic group on tyrosine

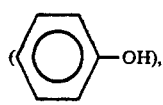

then an appropriate linking moiety is a diazo group (-N=N-). This linkage can readily be formed as follows:

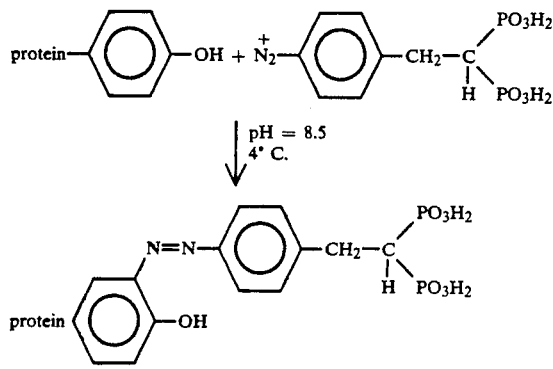

When the reactive end group contains a primary amine, such as the amino terminus or the epsilon amino group of lysine, an appropriate linking group would be, for example, an amide

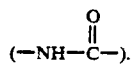

This linkage can readily be formed as follows:

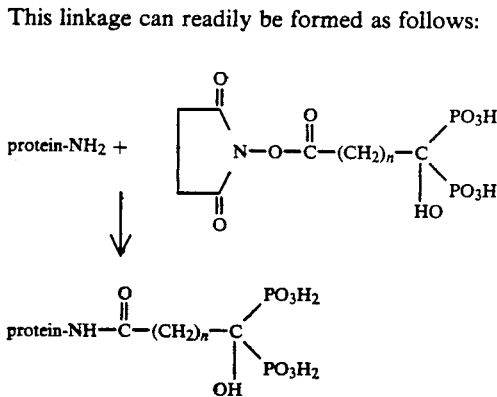

Other appropriate linking moieties where the reactive side chain contains a primary amine include a thiourea

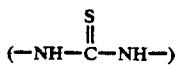

generated from a phenylisothiocyanate diphosphonate,

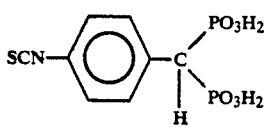

which reacts with a protein to form:

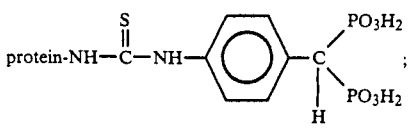

a sulfonamide linkage

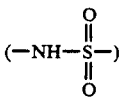

occurs by the reaction of an aryl sulfonyl halide containing diphosphonate,

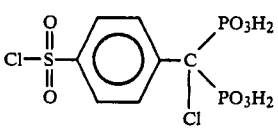

which reacts with the protein to form:

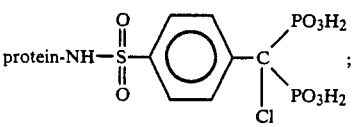

an N-carboxyanhydride-containing geminal diphosphonate,

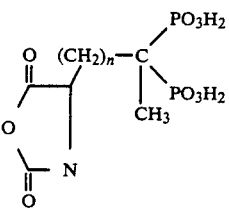

reacts with an amine containing protein to form an amide linkage

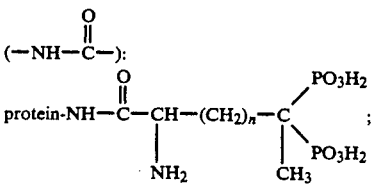

an imidate-containing geminal diphosphonate,

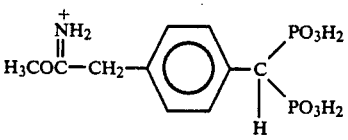

reacts with a protein to form an amidine (—HN—C(=NH)—) link:

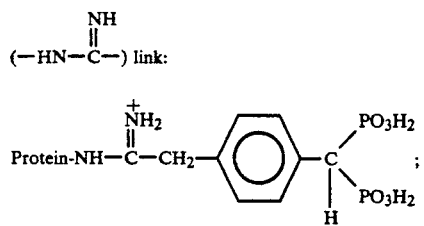

a quinone-diphosphonate can form a disubstituted hydroquinone link as follows:

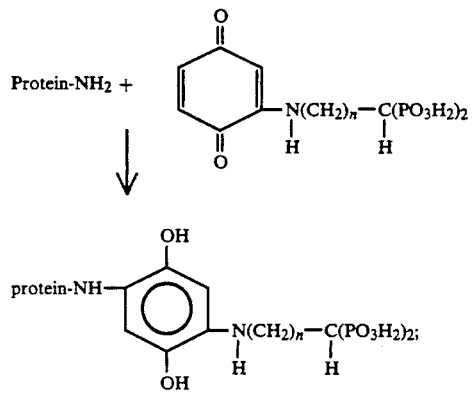

Schiff base chemistry via an aldehyde-diphosphonate,

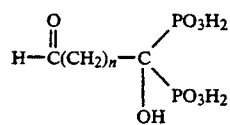

reacts with a protein to form an imine (-N=CH-) link. Reduction of the imine linkage yields:

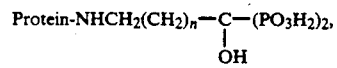

which contains an alkylamine linkage.

When the reactive side chain of the protein contains a carboxylic acid, as in aspartic or glutamic acid residues or "C" terminus, the appropriate diphosphonate contains an amino group which reacts with the protein to form an amide. This linkage can be formed by preactivating the protein carboxy group with a water-soluble carbodiimide, then coupling the reactive intermediate with an omega-aminoalkyldiphosphonate, such as:

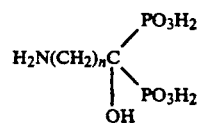

forming an amide (—NH—C(=O)—)

linkage when reacted with a protein:

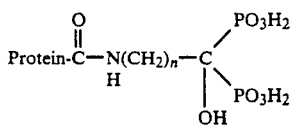

When the reactive group on the protein is a thiol (SH), as in crystene, then an appropriate diphosphonate contains an alkyl halide, for example,

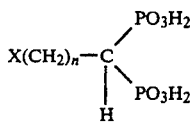

wherein X=Br or I.

This diphosphonate reacts with the thiol on the protein to form a thioether linkage (-CH$_2$-S-CH$_2$-):

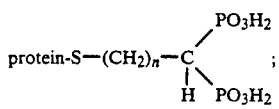

iodoacetyl diphosphonates such as

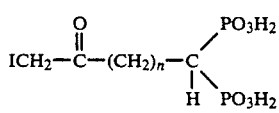

reacts with the thiol group on the protein to form a thioether linkage (-CH$_2$-S-CH$_2$-):

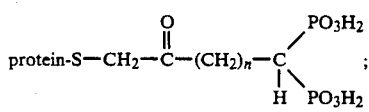

maleimide diphosphonates, such as

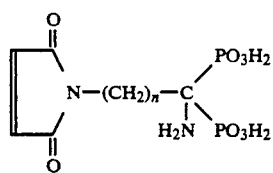

react with sulfhydryl-containing proteins to form a thioether linkage:

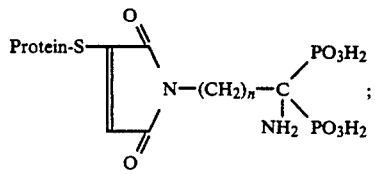

A disulfide linking group can be formed by reacting a 2-pyridine disulfide agarose gel with a sulfhydryl-containing diphosphonate to form a disulfide link (-S—S-) as follows:

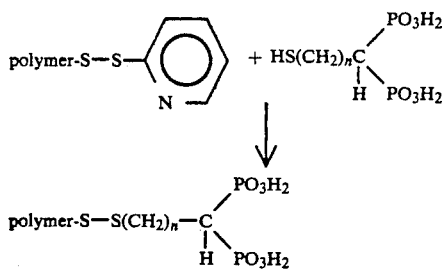

A carbamate linking group can be formed by a polysaccharide, such as reacting Sepherose$^R$ or Ficol$^R$ (Pharmacia Corporation), with cyanogen bromide to form a reactive imidocarbonate intermediate. A terminal amino-containing diphosphonate will react with the imidocarbonate intermediate to form a substituted carbamate product as follows:

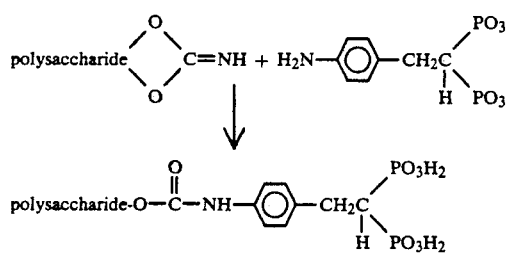

The spacer, Q, if needed, creates a space between the protein and the diphosphonate to permit the diphosphonate to be more accessible for radiolabeling. Suitable spacing groups are disclosed in Methods of Enzymology, Vol. 34 pp. 26–27, incorporated herein by reference. The spacer can be aryl or $C_1$ to $C_{12}$ alkyl. The aryl can be substituted or unsubstituted with one or more substituents. Preferred is an unsubstituted aryl.

The diphosphonate moieties utilized in the present invention (hereinafter diphosphonates) have the formula:

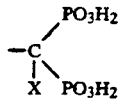

where X is H, OH, $NH_2$, substituted amino, halogen or $C_1$–$C_4$ alkyl, preferred is H, OH or substituted or unsubstituted amino.

These diphosphonates are useful as anticalcification agents for bioprosthetic devices and soft contact lenses. Bioprosthetic devices are known to undergo biological mineralization, generally this mineral component is composed of calcium phosphate. When this calcium builds up, the function of the device is impaired. The diphosphonate-derivatized macromolecules of the present invention when linked to such devices inhibit mineralization.

Diphosphonates can be attached to proteins, such as collagen, in heart valve and vascular graft implants. For example a water soluble carbodiimide is added to collagen for activation, this activated intermediate,

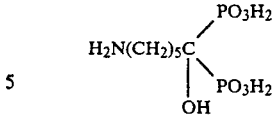

is then reacted with collagen to form:

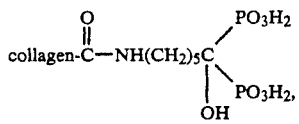

a diphosphonate-derivatized insoluble protein which will resist biological mineralization.

Covalent attachment of diphosphonates to extended wear soft contact lenses inhibit their calcification. These soft lenses are often composed of poly(acrylamides), polyols or polycarboxylates. The lens polymer can be reacted with a water soluble carbodimide, for example:

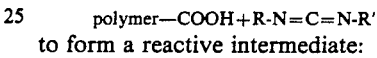

to form a reactive intermediate:

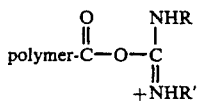

This intermediate can then be reacted with a diphosphonate to form a diphosphonate-derivatized polymer:

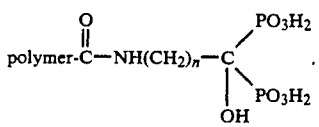

SCINTIGRAPHIC IMAGING AGENT

The diphosphonate-dervatized macromolecules are useful as scintigraphic imaging agents when chelated with technetium-99 m. Methods of labeling the phosphonate moiety. with Tc-99 m are disclosed in Castronovo et al., "The Phosphonate Moiety: Labeling with 99 m-Tc(Sn) After Synthetic Attachment to Diverse Biological Compounds", *Radiopharm.* [International Symposium], Chapter 7, pp. 63–70 (1975), incorporated herein by reference.

Generally, the diphosphonate-derivatized macromolecule is treated with a solution containing stannous ion. To this mixture is added a solution of Tc-99 m as pertechnetate. The Tc-99 m is reduced by the stannous ion forming a coordinate covalent linkage with the diphosphonate.

As used herein the term "pertechnetate reducing agent" includes compounds, complexes or the like, comprising a reducing ion capable of reducing heptavalent technetium ($TcO_4^-$) to trivalent, tetravalent and/or pentavalent technetium. Free metals, such as tin, are also known for use as pertechnetate reducing agents, although undissolved metal must be removed from the scanning solution prior to injection into the patient. Suitable pertechnetate reducing agents include sodium hydrosulfite, as well as metalic salts of sulfuric acid and hydrochloric acid, such as stannous chloride.

The compositions herein optionally, and preferably, contain a stabilizing amount of a stabilizer material to prevent or inhibit the oxidation of the pertechnetate reducing agent (e.g., oxidation of $Sn^{+2}$ to $Sn^{+4}$) during storage and/or to inhibit or diminish the reoxidation of reduced technetium-99 m and/or to diminish the formation of technetium-labeled impurities which may form during use of the compositions.

The stabilizers used herein are characterized by their toxicological acceptability under the conditions of use, their ability to stabilize the product for a reasonable period of storage and/or under usage conditions, and by their substantial non-interference with the delivery of the technetium radionuclide to, for example, soft tumors.

Stabilizers which meet the foregoing requirements and which are suitable for intravenous injection include gentisic acid and its water-soluble salts and esters, ascorbic acid and its water-soluble salts and esters, and erythorbic acid and its water-soluble salts and esters. Gentisic acid, ascorbic acid and erythorbic acid are all known, commercially-available materials. The sodium salts of these acids are also all commercially-available, quite water-soluble, and preferred for use herein.

As is known in the literature, stabilizer materials such as ascorbic acid can chelate or complex with technetium and cause it to be deposited in uncalcified soft tissue. Since the practitioner of the present invention will wish to avoid all unnecessary deposition in soft tissue, it will be appreciated that the amount of stabilizer materials optionally used in the present compositions should not be soggreat as to overshadow the tumor directing effect of the derivatized macromolecule, thereby interfering with the imaging.

The scintigraphic imaging agents of the present invention are intended for systemic or oral administration into humans or lower animals. Accordingly, appropriate manufacturing and operating conditions are employed to provide suitably sterile compositions.

For gastrointestinal imaging, oral administration would be the appropriate method of administration. For soft tissue tumor imaging, the appropriate route of administration would be intravascular or intralymphatic. For blood pool imaging, intravenous administration would be the appropriate method.

The compositions of the present invention can be prepared by simply dry mixing the technetium reducing agent and the derivatized macromolecule. The optional stabilizer can also be dry blended into such mixtures, as can additional, non-interferring agents, such as sodium chloride.

In an alternate mode, the compositions herein can be provided in lyophilized form. Such compositions are prepared by co-dissolving the diphosphonate-derivatized macrmmolecule and the technetium reducing agent in an aqueous solution, together with any desired optional stabilizers, and lypholizing the composition using standard equipment. Preferably, sterile, deoxygenated water is used in processing and the product is stored under nitrogen. Although somewhat more complicated to manufacture than the dry mixed product, the lypholized product offers the advantage that water-insoluble particulate matter which might be present in the raw materials can be removed by filtration prior to the freeze drying step.

In another mode, the compositions herein can be provided as aqueous solutions in phrmaceutically-acceptable liquid carriers. These carriers can be, for example, saline solution or sterile, pyrogen-free water. Preferably, the water is deoxygenated and the composition is stored under nitrogen, thereby minimizing undesirable oxidation of the pertechnetate reducing agent on storage. Since the reducing agent is more prone to oxidize in solution than in the dry powder and freeze-dried composition forms, it is preferred that aqueous compositions contain a stabilizer.

The compositions of the present invention are prepared such that the weight ratio of the derivatized macromolecule: technetium reducing agent is from about 2:1 to about 100,000:1, preferably from about 2:1 to about 10,000:1.

Stabilized compositions are generally formulated such that the weight ratio of derivatized macromolecule: stabilizer is from about 1:1 to about 10,000:1, preferably from about 1:1 to about 1,000:1.

Preferred stabilized compositions in unit dosage form contain from about 0.05 mg. to about 3 mg. of the stannous reducing agent; from about 0.25 mg. to about 1.0 mg. of the gentisate or ascorbate stabilizer; and from about 0.01 to about 50 mg. of the diphosphonate-derivatized macromolecule.

Compositions of the foregoing type are characterized by a physiologically-acceptable in-use solution pH in the range from about 3.5 to about 8.5, and, preferably, fall within a pH range of about 4.5 to about 7.4.

In the case of proteins, a liquid pharmaceutical composition suitable for scintigraphic imaging would be composed of from about 0.01% to about 20% of the diphosphonate-derivatized protein with the remainder being pertechnetate reducing agent, stabilizer, and a pharmaceutically-acceptable carrier. In the case of other macromolecules, from about 1% to about 20% of the total composition would be comprised of the diphosphonate-dervatized macromolecule.

In the case of proteins, a lyophilized pharmaceutical composition would be composed of from about 1% to about 50% of the diphosphonate-derivatized protein. For other macromolecules, from about 5% to about 99% of the composition would be comprised of the diphosphonate-derivatized macromolecule.

In use, the compositions are mixed with a pertechnetate-99 m isotonic solution from a commercial technetium source to yield a Tc-99 m labeled diphosphonate-derivatized macromolecule suitable for systemic or oral administration. The stability of such scanning agents is ample under ordinary hospital conditions. Administration is preferably done within about eight hours after addition of the pertechnetate solution. For intravenous administration, the concentration of reagents and technetium radionuclide is sufficient such that about 1 ml. of the solution is administered to an adult of about 50–100 kg. body weight. One ml. of solution is preferably injected intravenously over a period of about 30 seconds. For oral administration, the concentration of reagents and technetium radionuclide is sufficient such that from about 10 ml to about 150 ml of the solution or suspension is administered to an adult of about 50–100 kg body weight. Follow up scans would consist of the same levels of administration.

The actual structure of the reaction product formed by the 99 m Tc/diphosphonate-derivatized macromolecule reducing agent mixture and introduced into the body is not known with certainty.

These diphosphonate-derivatized macromolecules are useful for any bio-analytical technique where radiolabeled proteins would be used. Such applications include tumor imaging, radioimmunoassays, myrocardiol infarction assays, thrombosis imaging, receptor binding assays and blood pool imaging, and gastrointestinal imaging.

Generally, a safe and effective amount of the radiolabeled macromolecule is administerd systemically or orally for the scintigraphic imaging procedures of the present invention.

By "safe and effective amount" as used herein is meant an amount of the composition high enough to provide a clinically useful scintigraphic image, but low enough to avoid serious side effects (at a reasonable benefit/risk ratio), within the scope of sound medical judgment. The safe and effective amount of the composition will vary with the particular scintigraph technique and particular clinical condition being evaluated, the age and physical condition of the patient being treated, the severity of the condition, the duration of treatment, the nature of concurrent therapy and the specific diphosphonate-derivatized macromolecule employed.

Systemic administration would be appropriate for tumor imaging, myrocardial infarction assays, thrombosis imaging, receptor binding assays, and blood pool imaging.

The following nonlimiting examples illustrate the compounds, chelates, compositions, methods and uses of the present invention.

EXAMPLE I

This example demonstrates, protein derivatization of sodium [2-(4 aminophenyl)-ethane 1,1-diphosphonate].

Sodium [2-(4-aminophenyl) ethane-1,1-diphosphonate] was synthesized by the following method:

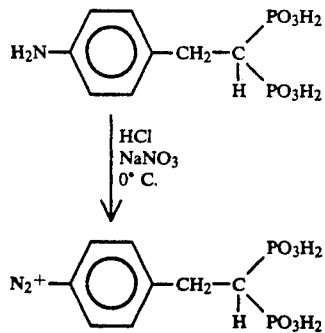

Specifically, to a slurry of 10.0 g (0.25 mole) of potassium hydride in 200 ml dry. toluene, cooled to 5° C., was added dropwise 72.5 g (0.25 mole) of tetraethyl methanediphosphonate. This reaction was carried out under a nitrogen atmosphere allowing the hydrogen gas generated to be swept away. The diphosphonate anion solution was brought to room temperature after all the ester had been added. 54 grams (0.25 mole) of p-nitrobenzylbromide was dissolved in 200 ml warm, dry toluene. The toluene solution of the halide was added rapidly to the diphosphonate anion solution. The reaction was somewhat exothermic causing a temperature rise to 85° C. The mixture was stirred at room temperature for 2 hours. The KBr that formed was filtered off and the toluene evaporated on a rotary evaporator. Then 250 ml of water was added to the remaining oil and the mixture extracted 2 times with 250 ml diethyl ether. The ether phase was dried with anhydrous magnesium sulfate, filtered and evaporated. The resulting oil was dissolved in 250 ml of ether and the solution was extracted 2 times with 100 ml water to remove the unreacted tetraethylmethane diphosphonate which is quite water soluble. The ether layer was dried with magnesium sulfate and evaporated yielding 76 grams of the crude ester: tetraethyl 2-(p-nitrophenyl)-ethane-1,1-diphosphonate.

Twenty-two grams of this crude ester was added to 250 ml ethanol in a 500 ml Parr hydrogenation bottle. A 10% Pd/charcoal catalyst (1.5 g) was added and the mixture was shaken under a 50 psig hydrogen atmosphere repressurizing as necessary. After 4.5 hours, the reaction was complete. The solid was filtered off and the ethanol evaporated. Two hundred fifty ml of 6N HCl was added to this crude product that contained a mixture of mono- and dialkylated methanediphosphonate. The mixture was refluxed overnight. The reaction mixture was cooled and evaporated to dryness on a rotary evaporator. Two hundred ml distilled water was added to the residue. The mixture was warmed to approximately 60° C. for 1 hour and then cooled to room temperature. A substantial amount of insoluble precipitate remained. This is the desired product. It was filtered off and slurried in 150 ml of water. The pH was adjusted to 4.2 with 50% sodium hydroxyide solution. The solution was heated to boiling and filtered hot. Two hundred ml of ethanol was added slowly to the warm solution causing a precipitate to develop. This solution was cooled in a refrigerator overnight. The precipitate, the sodium salt of the desired product, was filtered off, washed with methanol and air dried. The result was 6.2 grams of sodium -[2-(4-amino phenyl)-ethane-1,1-diphosphonate].

The sodium [2-(4-aminophenyl)-ethane-1, 1-diphosphonate-](0.3 mg, 0.1 mmol) was dissolved in 0.5 ml of $H_2O$, chilled in an ice-bath, and then acidified with 0.5 ml of concentrated HCl. To this clear solution was added dropwise 0.25 ml of chilled 0.5M (0.125 mmole) $NaNO_2$ solution. The pale yellow solution was stirred for 1.5 hour at 0° C., then treated with 3 mg of urea to destroy excess nitrate. The reaction mixture was then diluted to 10 ml. The desired amount of diazonium salt reagent was removed from this stock solution, neutralized with solid $NaHCO_3$, and added dropwise to a 0° C. solution of rabbit IgG (obtained from Sigma Chemical Corporation) (60 mg) in 3 ml of 0.05 $\underline{M}$ pH8 phosphate buffer. The reaction mixture was stirred overnight at 4° C., then dialyzed exhaustively against 0.1M NaCl solution at 4° C. The solution of derivatized protein was stored in the refrigerator.

The resultant solution of derivatized protein was analyzed according to the standard Biyret analysis for determining protein concentration as disclosed in Bulletin #690, Sigma Chemical Co., St. Louis, Mo.

The degree of derivatization, in terms of average number of azo groups in the derivatized protein solution, was calculated from the solution's absorbance at 350 nm (E=20,000). The protein concentration was determined from its characteristic absorbance at 280 nm. It was necessary to make a slight correction for the protein concentration due to small degree of absorbance of the azo phenyl group at 280 nm (E=19,800). The ratio of azo concentration to the corrected protein concentration then gives the average number of azo linkages per protein molecule.

The number of azo groups per protein molecule was calculated as follows:

For the derivatization of rabbit IgG using a molar ratio of 25:1 diazonium salt to protein, the following procedure was used to determine the average number of diphosphonate groups bound to each protein molecule.

Measured absorbances: $A_{350}=0.262$, $A_{280}=1.546$

Calculation of azo concentration: ($E_m$ for azo=22,000)

at 350 nm: $A=0.262=22,000 \times C_{azo}$ $C_{azo}=1.19 \times 10^{-5} \underline{M}$ Calculation of azo phenyl absorbance at 280 nm: $E_m$ for azo phenyl=19,800)

$A = 19,800 \times 1.19 \times 10^{-5}\underline{M}=0.236$

Calculation of protein concentration ($A_{280}$ for rabbit IgG=219,000):

$A=1.546-0.236=1.31=219,000 \times C_{protein}$ $C_{protein}=5.98 \times 10^{-}\underline{M}$ Calculation of azo group per protein molecule $$\frac{\text{number of azo groups}}{\text{per protein molecule}} = \frac{1.19 \times 10^{-5}}{5.98 \times 10^{-6}} = 1.99$$

EXAMPLE II

The following example illustrates the binding of technetium -99 m to diphosphonate-dervatized IgG and F(ab')2 fragments.

Rabbit IgG (obtained from Sigma Corporation) was derivatized amd labeled with 99 m-Tc as described in Example III except without gentisic acid. Between 2 and 3 mg of IgG or derivatized IgG were labeled with 500μCi 99 m-TC. The reaction mixture was gel filtered over a column of BioGel P6 (Bio Rad) and 1.0 mg of the peak protein fractions were taken for the following plasma exchange experiments.

An aliquot of 99 m-Tc labeled DP derivatized IgG was added to 1.0 ml of freshly prepared heparinized human plasma. Underivatized, 99 m-Tc labeled IgG was treated identically and used as a control. The combined IgG-plasma was heated at 37° with continuous agitation. After 30 minutes, an excess of goat anti-rabbit γ-globulin (GARGG) was added to precipitate the rabbit IgG. Following centrifugation, the rabbit IgG precipitate and the plasma supernatant were subjected to γ-counting. Any 99 m-Tc which remained associated with the rabbit IgG wa found in the precipitate. The results are summarized in the following Table:

| mole DP per mole IgG | 99m-Tc bound per mg IgG (counts/100 sec) | % 99mTc which does not exchange with plasma components |
| --- | --- | --- |
| 0 | $1.13 \times 10^5$ | 37% |
| 0.3 | $3.47 \times 10^5$ | 84% |
| 1.9 | $3.82 \times 10^5$ | 87% |
| 8.0 | $4.81 \times 10^5$ | 91% |

The diphosphonate-derivatization procedure of the present invention does not significantly alter the activity of the antibody as estimated by these competitive binding studies. The addition of the diphosphonate did increase the affinity of antibodies for binding with 99 m-Tc.

These data demonstrate that DP-IgG not only binds more 99 m-Tc than does underivatized IgG, but the 99 m-Tc is bound more tightly to DP-IgG as judged by the high percentage of 99 m-Tc which does not dissociate from DP-IgG. Substantially similar results are obtained when F(ab)2 fragments rather than IgG fragments were characterized.

EXAMPLE III

This example illustrates in vivo imaging of soft tissue tumor using DP-IgG and DP-F(ab')2

IgG and F(ab')2 fragments were prepared from commercially available rabbit antisera to human $\beta_2M$ and human CEA. For CEA, the IgG fraction as prepared by the supplier was used, while rabbit anti $\beta_2M$ was further purified using an affinity column of immobilized human $\beta_2M$.

IgG and F(ab')2 fragments were derivatized as described above in Example I. The stoichiometric ratio of the reactants, diphosphonate: protein, was 10:1. After exhaustive dialysis against phosphate buffered saline at pH 7.4, 1.0 mg each of IgG and F(ab')2 fragment were freeze-dried.

In preparation for labeling with 99 m-Tc and injection, the freeze-dried proteins wre dissolved in 700 μl sterile H2O. One hundred twenty-five micrograms of gentisic acid, 4 mCi Tc-99 m as $TcO_4^-$, and 250 μg SnCl2 were then added to each vial. Injections of 220-250 μl were made into the tail vein of athymic mice bearing either a human colonic carcinoma tumor which expresses CEA, or a human prostatic carcinoma tumor which express $\beta_2M$. Scintigraphs were obtained on a Technicare Sigma 400 gamma camera at 1, 4 and 24 hours post-injection using a pinhole columnator. At 24 hours after dosing, animals receiving anti $\beta_2M$ IgG and F(ab')2 fragments were sacrificed, tumors excised and half of each tumor was fixed in 10% neutral buffered formalin. The other half of each tumor was embedded and frozen for indirect immunofluorescence.

At 4 hours post-injection the anti $\beta_2M$ IgG and its F(ab')2 fragments showed good tumor localization.

Immunohistochemical evaluation of the tumors, excised 24 hours after injection of the IgG or F(ab')2 fragments, demonstrated that the IgG and F(ab')2 fragments did reach the tumor.

EXAMPLE IV

This example demonstrates the use of a diphosphonate-derivatized insoluble macromolecule for use as a gastrointestinal imaging agent.

10 g Sepherose CL-4B (a polysaccharide obtained from Pharmacia Corporation) was added to 10 ml distilled H2O. The sample was activated in 2M Na2CO3 solution using cyanogen bromide dissolved in acetonitrile (2 g. CNBr/ml CH3CN). The Sepherose was stirred vigorously at room temperature for 2 minutes. The resin was filtered off, washed with 0.1 N NaHCO3 pH=9.5 and then with H2O. The activated gel was added to 30 ml 0.2M NaHCO3 pH 9.7 to which 1.5 g 2-(4-aminophenyl) ethane-1,1-diphosphonic acid had been added. This mixture was reacted overnight in a refrigerator ( 4° C.) The gel was filtered off. 2M glycine was added at pH=9.5 to the gel (to quench the unreacted sites). The derivatized gel was then washed with excess water. The pH of the slurry was adjusted to 5.0 with hydrochloric acid.

To test for Tc-99 m binding to the gel, the following experiment was carried out:

0.5 g derivatized CL-4B was mixed with 3 ml distilled water and 50 μl of a stock solution of 120 mg. $SNCl_2 \cdot 2H_2O$ dissolved in 5 ml 0.1 N HCl. To this slurry was added 240 Ci Tc-99 m $TcO_4^-$ solution in saline. The vial was shaken for 2-3 minutes and then filtered through a 0.45 syringe filter.

The activity in the syringe and filter as well as in the filtrate was measured. 97.5% of the technetium remained associated with the gel. A control experiment using underivatized Sepherose$^R$ CL-4B was run as described above and only 21.6% of the technetium remained associated with the gel.

EXAMPLE V

This example demonstrates formation of a diphosphonate-derivatized polysaccharide gel containing a disulfide linking group.

A (glutathione-2-pyridyl disulfide) agarose conjugate is prepared as described in Methods in Enzymology 34 pp 536-538. This gel (Agarose-GS-2 pyridyl) is reacted with an excess of 4-mercaptobutane-1,1-diphosphonate in phosphate buffered soluton at pH=8. After reaction, the gel is washed exhaustively on a glass filter using isotonic saline.

The product formed is:

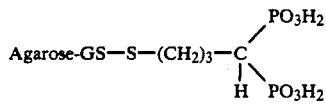

EXAMPLE VI

This example demonstrates formation of a diphosphonate-derivatized albumin containing a thiourea linkage suitable for use in a lung imaging formulation.

The 2-(4-aminophenyl)ethane-1,1-diphosphonate described in Example I is converted to 2-(4-isothiocyanatophenyl)ethane-1,1-diphosphonate by treatment with a 10 fold molar excess of thiophosgene in 0.4M $NaHCO_3$ aqueous buffer at room temperature. The reaction solution is extracted with dichloromethane to remove unreacted thiphosgene. This isothiocyanate diphosphonate-containing solution is reacted with a suspension of aggregated albumin particles, 15 mg of albumin (10μ-100μ diameter) in 25 ml 0.4M $NaHCO_3$ buffer, pH=8.5, for 60 minutes at 37° C. Following reaction the diphosphonate-derivatized albumin aggregates are collected and washed by centrifugation to remove untreated diphosphonate.

The product formed is:

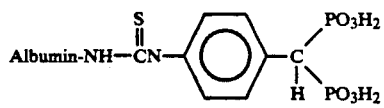

EXAMPLE VII

The example demonstrates photo-induced coupling of a diphosphonate to an antibody fragment.

The diazophenylethane-1,1-diphosphonate described in Example I is converted to 2-(4-azophenyl)-ethane-1,1-diphosphonate by treatment with an aqueous solution of sodium azide at pH=9 and 4° C. The product is recovered by precipitation from the reaction solution with ethanol. One mg of F(ab')$_2$ fragment of anti-β$_2$M macroglobulin described in Example I is mixed with 10 mg of the above azidophenyl diphosphonate dissolved in 5 ml of phosphate buffered saline at 4° C. Irradiation is carried out using a Rayonet Minireactor at 240-350 nm. The nitrene intermediate formed upon photolysis couples to the protein molecules. Following reaction the excess diphosphonate is removed by gel permeation chromatography on a Sephadex G-25 column.

EXAMPLE VIII

Aminoethyl cellulose previously washed with 0.5M NaOH and water is suspended in 0.05M phosphate buffer pH=7 (10 g dry weight in 250 ml). Twenty ml of a 25% w/v solution of glutaraldehyde is added. After 2 hr of stirring at room temperature, the cellulose derivative is recovered by filtration and washed with water. The product is resuspended in the same buffer and treated with 2.0 g of 5-aminopentane-1-hydroxy-1,1-diphosphonate. After stirring at room temperature for 3 hours, the cellulose is recovered by filtration and washed exhaustively with water to remove the untreated diphosphonate.

The product formed is:

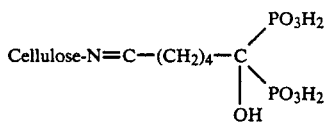

EXAMPLE IX

The diphosphonate-derivatized aminoethyl cellulose from Example VIII is treated with an aqueous solution of sodium borohydride at pH=9.5. This chemical reduction process stabilizes the imine linkage formed in Example VIII yielding a more stable dialkylamine linkage.

The product formed is:

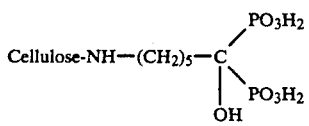

EXAMPLE X

A clear hydrogel copolymer film containing poly(hydroxyalkyl methacrylate) is suspended in borate buffer that is 10% w/v in cyanogen bromide buffer at pH=11. The pH is maintained at pH=11 with 4N NaOH solution. After activation with cyanogen bromide, the polymer film is treated overnight with a 50 mmolar solution of 6-amino-1-hydroxyhexane-1,1-diphosphonate at pH=9 in 0.5 M NaHCO$_3$ buffer. The derivatized polymer film is washed exhaustively in distilled water to remove unreacted diphosphonate.

The product formed is:

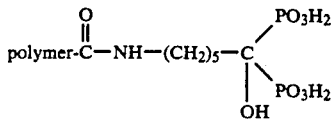

What is claimed is:

1. Diphosphonate-derivatized macromolecules of the formula

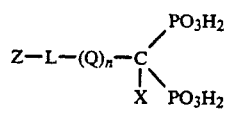

wherein
Z is a macromolecule selected from the group consisting of proteins and polypestides and further contains one or more reactive end groups selected from the group consisting of $-NH_2$, $-COOH$, $-SH$, $CHO$, $-S-S$, $-OH$, phenol, guanidino, imidazole or indole, and mixtures thereof;
L is a linking moiety selected from the group consisting of

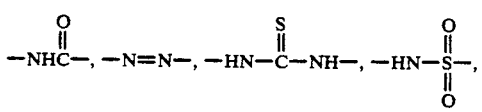

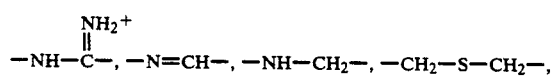

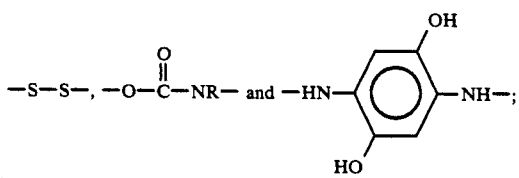

Q is a spacing group selected from the group consisting of $C_1-C_{12}$ alkyl substituted aryl, unsubstituted aryl or $C_1$ to $C_{12}$ alkyl, where n is 0 or 1; and X is selected from the group consisting of H, OH, $NH_2$, $C_1-C_{12}$ alkyl substituted or unsubstituted amino, halogen or $C_1-C_4$ alkyl; and the pharmaceutically-acceptable salts of these derivatized macromolecules.

2. The diphosphonate-derivatized macromolecules according to claim 1 wherein said protein is an antibody or antibody fragment.

3. The diphosphonate-derivatized macromolecules according to claim 1 wherein said linking moiety is selected from the group consisting of

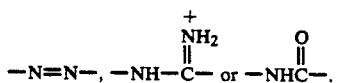

4. The diphosphonate-derivatized macromolecules according to claim 3 wherein said spacing group is an unsubstituted aryl.

5. The diphosphonate-derivatized macromolecules according to claim 4 wherein X is selected from the group consisting of H, OH or $NH_2$.

6. The diphosphonate-derivatized macromolecules according to claim 1 selected from the group consisting of

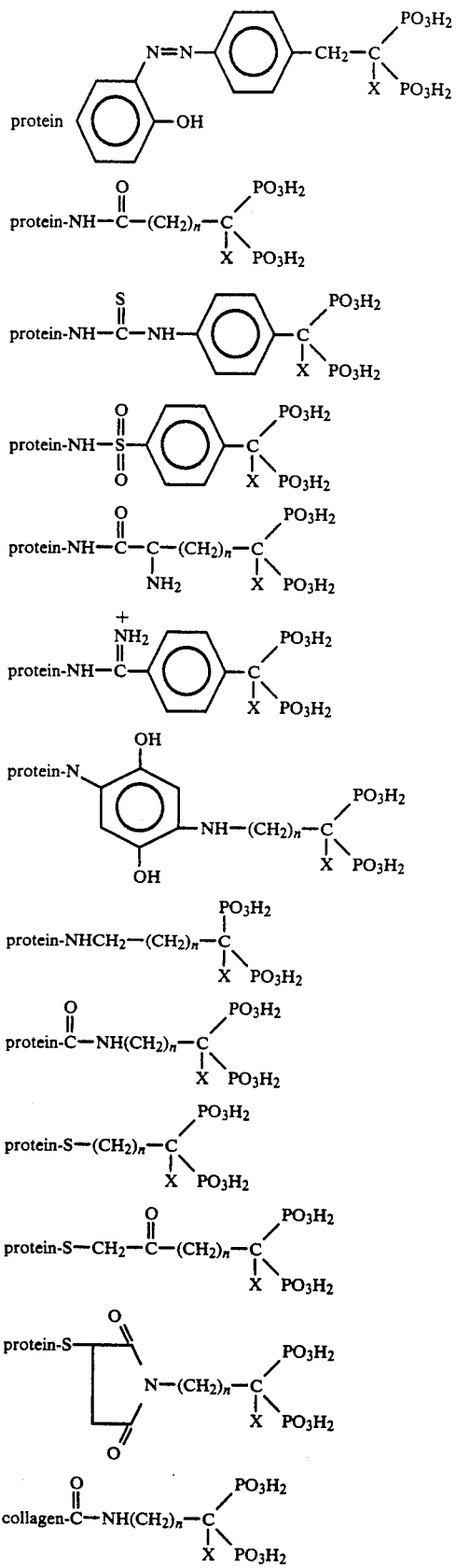

wherein n is an integer from 0 to about 12; and X is selected from the group consisting of H, OH and $NH_2$.

* * * * *